United States Patent
Banerjee et al.

(10) Patent No.: US 9,855,012 B2
(45) Date of Patent: Jan. 2, 2018

(54) METHOD AND SYSTEM FOR NOISE CLEANING OF PHOTOPLETHYSMOGRAM SIGNALS

(71) Applicant: Tata Consultancy Services Limited, Mumbai (IN)

(72) Inventors: Rohan Banerjee, Kolkata (IN); Anirban Dutta Choudhury, Kolkata (IN); Aniruddha Sinha, Kolkata (IN); Avik Ghose, Kolkata (IN); Arpan Pal, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 104 days.

(21) Appl. No.: 15/073,232

(22) Filed: Mar. 17, 2016

(65) Prior Publication Data

US 2016/0310084 A1 Oct. 27, 2016

(30) Foreign Application Priority Data

Apr. 27, 2015 (IN) .......................... 1684/MUM/2015

(51) Int. Cl.
| | |
|---|---|
| *G06K 9/00* | (2006.01) |
| *A61B 5/00* | (2006.01) |
| *A61B 5/021* | (2006.01) |
| *G06T 5/00* | (2006.01) |
| *G06T 5/20* | (2006.01) |
| *G06T 7/00* | (2017.01) |
| *A61B 5/024* | (2006.01) |

(52) U.S. Cl.
CPC .......... *A61B 5/7235* (2013.01); *A61B 5/0059* (2013.01); *A61B 5/0077* (2013.01);
(Continued)

(58) Field of Classification Search
CPC ..... A61B 5/0059; A61B 5/0077; A61B 5/021; A61B 5/02116; A61B 5/02438
(Continued)

(56) References Cited

U.S. PATENT DOCUMENTS 9,195,900 B2 * 11/2015 Gu ........................... G06K 9/46
9,662,022 B2 * 5/2017 Kyal .................. A61B 5/02405
(Continued)

FOREIGN PATENT DOCUMENTS

EP 2 544 125 A1 1/2013

OTHER PUBLICATIONS

Bolanos et al., "A PDA-based Electrocardiogram/Blood Pressure Telemonitor for Telemedicine" Proceedings of the 26th Annual International Conference of the IEEE Engineering in Medicine and Biology Society, 1 cover page and pp. 2169-2172, (2004) https://www.researchgate.net/profile/Homayoun_Nazeran/publication/6532846_A_PDA-based_electrocardiogramblood_pressure_telemonitor_for_telemedicine/links/54e238b10cf2edaea0926bde.pdf.

(Continued)

*Primary Examiner* — Charlotte M Baker
(74) *Attorney, Agent, or Firm* — Finnegan, Henderson, Farabow, Garrett & Dunner LLP

(57) ABSTRACT

A method and system is provided for noise cleaning of photoplethysmogram signals. The method and system is disclosed for noise cleaning of photoplethysmogram signals for estimating blood pressure of a user; wherein photoplethysmogram signals are extracting from the user; the extracted photoplethysmogram signals are up sampled; the up sampled photoplethysmogram signals are filtered; uneven baseline drift of each cycle is removed from the up sampled and filtered photoplethysmogram signals; outlier cycles of the photoplethysmogram signals are removed and remaining cycles of the photoplethysmogram signals are modeled; and time domain features are extracted from originally extracted and modeled photoplethysmogram signals for estimating blood pressure of the user.

23 Claims, 6 Drawing Sheets

(52) U.S. Cl.
CPC .......... *A61B 5/021* (2013.01); *A61B 5/02116* (2013.01); *A61B 5/7203* (2013.01); *A61B 5/7246* (2013.01); *A61B 5/7278* (2013.01); *G06T 5/002* (2013.01); *G06T 5/20* (2013.01); *G06T 7/0012* (2013.01); *A61B 5/02438* (2013.01); *A61B 5/6898* (2013.01); *A61B 5/7264* (2013.01); *G06T 2207/10016* (2013.01); *G06T 2207/20182* (2013.01); *G06T 2207/30104* (2013.01)

(58) Field of Classification Search
USPC ............. 382/128; 379/265.06; 600/310, 315, 600/324, 479, 323, 476, 480
See application file for complete search history.

(56) References Cited

U.S. PATENT DOCUMENTS

| | | |
|---|---|---|
| 2012/0190947 A1 | 7/2012 | Chon et al. |
| 2013/0072145 A1 | 3/2013 | Dantu |
| 2014/0031646 A1 | 1/2014 | Yakirevich et al. |
| 2016/0113531 A1* | 4/2016 | Visvanathan ...... A61B 5/02416 600/323 |
| 2016/0156779 A1* | 6/2016 | Deshmukh ............ G06T 7/0012 379/265.06 |
| 2016/0157761 A1* | 6/2016 | De Haan ............... A61B 5/0059 600/315 |
| 2017/0202505 A1* | 7/2017 | Kirenko ................. A61B 5/443 |

OTHER PUBLICATIONS

Jonathan et al., "Cellular phone-based photoplethysmographic imaging", Journal of Biophotonics, Wiley-VCH Verlag GmbH & Co. KGaA, Weinheim, cover page and pp. 1-4, (2010) https://www.researchgate.net/profile/Martin_Leahy/publication/46427616_investigating_a_smartphone_imaging_unit_for_photoplethysmography._Physiol_Meas_31N79-N83/links/53ce997b0cf2aada06e6a7e6.

\* cited by examiner

METHOD AND SYSTEM FOR NOISE CLEANING OF PHOTOPLETHYSMOGRAM SIGNALS

PRIORITY CLAIM

This U.S. patent application claims priority under 35 U.S.C. §119 to: India Application No. 1684/MUM/2015, filed on 27 Apr. 2015. The entire contents of the aforementioned application are incorporated herein by reference.

TECHNICAL FIELD

The present application generally relates to biomedical signal processing and more particularly to, a method and system for noise cleaning of photoplethysmogram (PPG) signals captured using a mobile communication device.

BACKGROUND

Recent time has witnessed tremendous growth in communication technology worldwide. Consequently, communication devices have started replacing manual human efforts in a big way. Particularly, communication devices such as smart phone and applications embedded therein for physiological sensing are rapidly gaining popularity in both developed and developing nations. Smart phone based physiological sensing applications provides both elderly as well as young adults with an opportunity to monitor numerous physiological vitals regularly at home for indicative and preventive measurements without possessing dedicated clinical devices.

In order to support various physiological sensing applications, smart phones of recent time are equipped with a plurality of inbuilt sensors such as accelerometer, microphone and camera. Accelerometer and microphone can be employed to measure certain physiological parameters such as breathing rate and heart rate, while smart phone camera may be utilized for estimating several vitals using photoplethysmography, which is a non-invasive technique to measure the instantaneous blood flow in capillaries. Since, capillary blood flow increases during systole and reduces during diastole. Thus, photoplethysmogram (PPG) signal of a person is periodic in nature, whose fundamental frequency indicates the heart rate. The photoplethysmogram (PPG) is further used for measuring several physiological vitals including heart rate, blood pressure, respiratory rate, blood oxygen saturation and certain ECG parameters.

Prior art literature illustrates a variety of solutions for estimating systolic (Ps) and diastolic (Pd) blood pressure from photoplethysmogram. Some of the prior art literature uses a combination of PPG and ECG signal for measuring the pulse transit time to estimate blood pressure. In another approach, photoplethysmogram signal, synchronized with a microphone can also be used to serve this purpose. It is important to observe that some of the prior art literature proposes a set of time domain photoplethysmogram features to estimate Ps and Pd using machine learning techniques; an indirect approach of estimating blood pressure could be via the R and C parameters of Windkesel model using photoplethysmogram features.

A majority of existing solutions used for measuring blood pressure using photoplethysmogram can be employed only when they are applied on clean and noise-free photoplethysmogram signal. However, such solution exhibit practical constraints when photoplethysmogram signals are captured using communication devices such as smart phones. Smart phones typically capture video at 30 fps, yielding a very low sampling rate of the extracted photoplethysmogram signal, which is 30 Hz compared to a clinical devices on 100 Hz or more. In addition to that, surrounding lights while capturing photoplethysmogram signals using smart phone also affect the signal quality. A little finger movement or even a variation in finger pressure can largely affect the photoplethysmogram signal quality, thereby the signal in time domain becomes more vulnerable and less reliable. Thus, photoplethysmogram signals captured using smart phones are noisy in nature. Although they have been successfully used to determine heart rate using frequency domain analysis, further indirect markers like blood pressure require time domain analysis for which the signal needs to be substantially cleaned. The existing prior art solution illustrates use of filters for noise cleaning of captured photoplethysmogram signals, which might not be sufficient for detailed noise cleaning and remove the undesired frequency. In turn, such filtering might not be enough to estimate vitals such as blood pressure.

Thus, in the light of the above mentioned background art, it is evident that, a method and system for noise cleaning of photoplethysmogram signals for estimating blood pressure of a user is desired.

SUMMARY

Embodiments of the present disclosure present technological improvements as solutions to one or more of the above-mentioned technical problems recognized by the inventors in conventional systems. For example, in one embodiment, a method for noise cleaning of photoplethysmogram signals for estimating blood pressure of a user. The method includes extracting photoplethysmogram signals from the user and up sampling the extracted photoplethysmogram signals. Further, the method includes, filtering the up sampled photoplethysmogram signals and then removing uneven baseline drift of each cycle of the up sampled and filtered photoplethysmogram signals. Subsequently, the method includes, removing outlier cycles of the photoplethysmogram signals by k-means clustering, modeling remaining cycles of the photoplethysmogram signals after removing outlier cycles with a sum of 2 Gaussian functions and then, extracting time domain features from originally extracted and modeled photoplethysmogram signals for estimating blood pressure of the user.

In another embodiment, a system for noise cleaning of photoplethysmogram signals for estimating blood pressure of a user is provided. The system comprises of an image capturing device coupled with a mobile communication device, an up sampling module, a filtering module, a baseline drift removal module, an outlier removing module, a signal modeling module, and a feature extraction module.

In yet another embodiment, a non-transitory computer-readable medium having embodied thereon a computer program for executing a method for noise cleaning of photoplethysmogram signals for estimating blood pressure of a user is provided. The method includes extracting photoplethysmogram signals from the user and up sampling the extracted photoplethysmogram signals. Further, the method includes, filtering the up sampled photoplethysmogram signals and then removing uneven baseline drift of each cycle of the up sampled and filtered photoplethysmogram signals. Subsequently, the method includes, removing outlier cycles of the photoplethysmogram signals by k-means clustering, modeling remaining cycles of the photoplethysmogram signals after removing outlier cycles with a sum of 2 Gaussian functions and then extracting time domain features from originally extracted and modeled photoplethysmogram signals for estimating blood pressure of the user.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
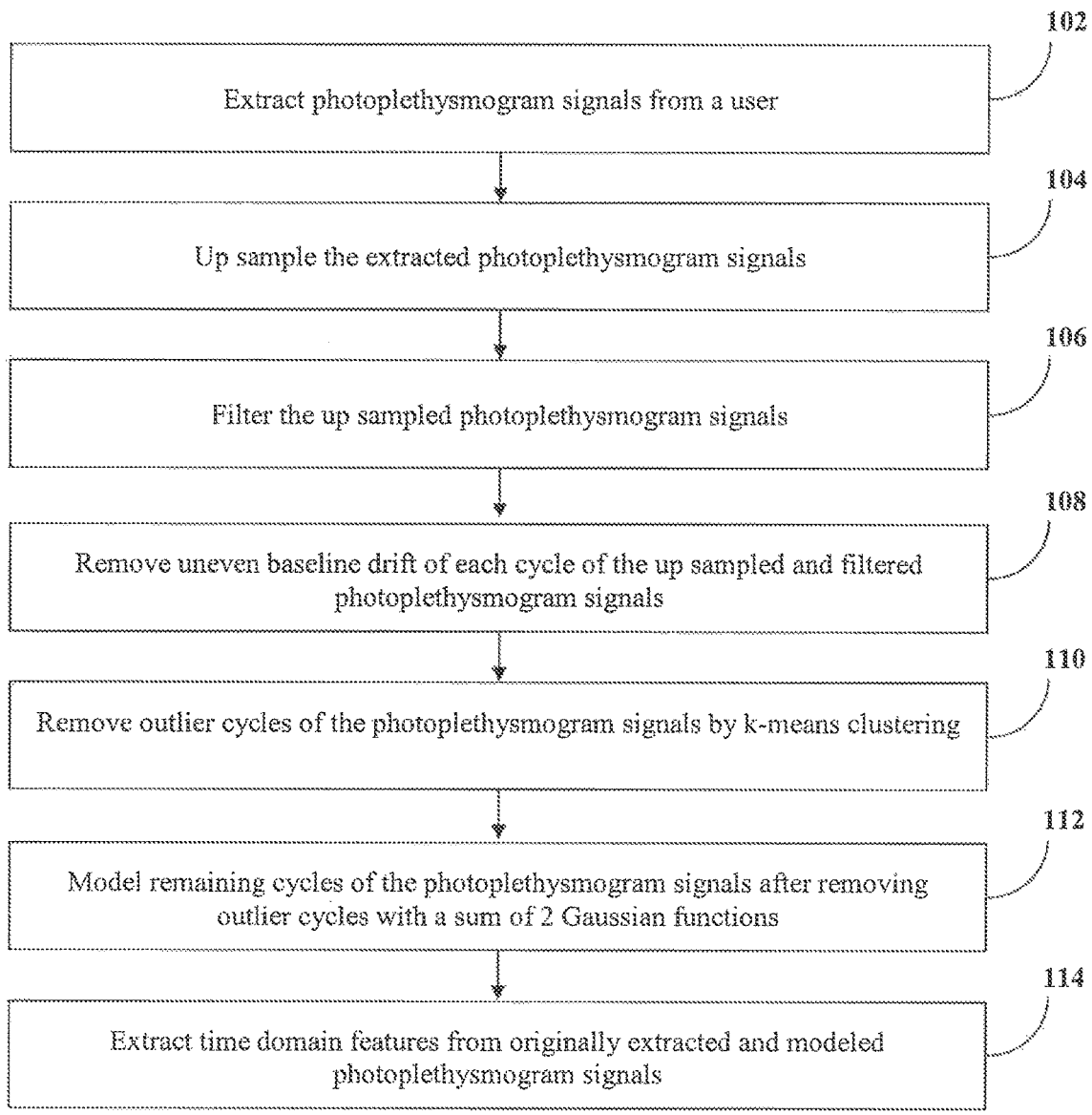
FIG. 1: shows a flow chart illustrating a method for noise cleaning of photoplethysmogram signals for estimating blood pressure of a user.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The disclosed embodiments are merely exemplary of the invention, which may be embodied in various forms.

The present invention enables a method and system for noise cleaning of photoplethysmogram (PPG) signals for estimating blood pressure (BP) of a user.

In an embodiment of the present invention, a system (200) for noise cleaning of photoplethysmogram signals for estimating blood pressure of a user comprises of an image capturing device (202) coupled with a mobile communication device (204); an up sampling module (206); a filtering module (208); a baseline drift removal module (210); an outlier removing module (212); a signal modeling module (214); and a feature extraction module (216).

Referring to FIG. 1 is a flow chart illustrating a method for noise cleaning of photoplethysmogram signals for estimating blood pressure of a user.

The process starts at step 102, photoplethysmogram signals are extracted from the user using the image capturing device (202) coupled with the mobile communication device (204). At the step 104, the extracted photoplethysmogram signals are up sampled using the up sampling module (206). At the step 106, the up sampled photoplethysmogram signals are filtered using the filtering module (208). At the step 108, uneven baseline drift of each cycle of the up sampled and filtered photoplethysmogram signals is removed using the baseline drift removal module (210). At the step 110, outlier cycles of the photoplethysmogram signals are removed by k-means clustering using the outlier removing module (212). At the step 112, remaining cycles of the photoplethysmogram signals after removing outlier cycles are modeled with a sum of 2 Gaussian functions using the signal modeling module (214). The process ends at the step 114, time domain features are extracted from originally extracted and modeled photoplethysmogram signals using the feature extraction module (216) for estimating blood pressure of the user.

Figure 2:
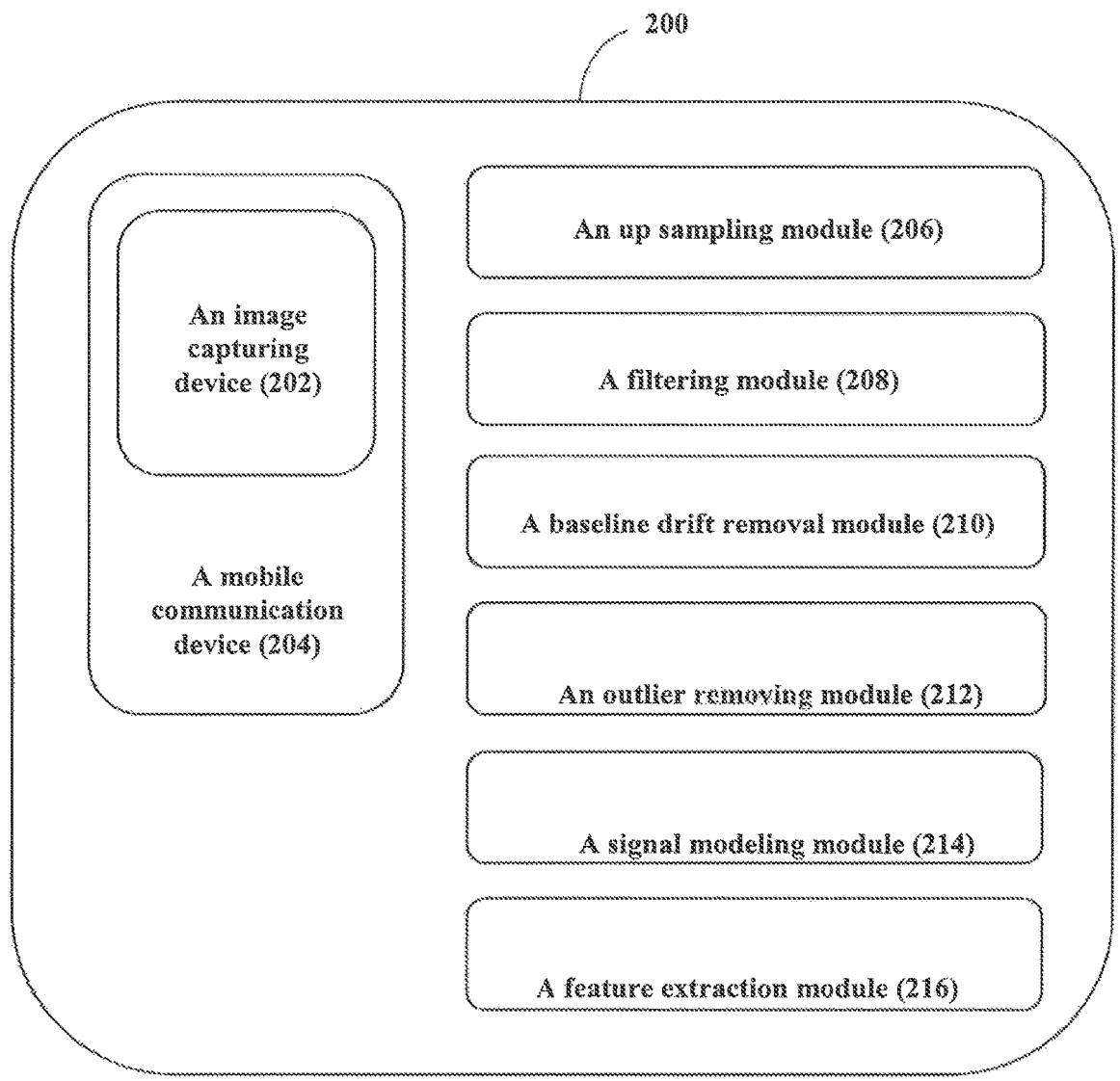
FIG. 2: shows a block diagram illustrating system architecture for noise cleaning of photoplethysmogram signals for estimating blood pressure of a user.

Referring to FIG. 2 is a Nock diagram illustrating system architecture for noise cleaning of photoplethysmogram signals for estimating blood pressure of a user.

In another embodiment of the present invention, the image capturing device (202) coupled with the mobile communication device (204) is adapted for extracting photoplethysmogram signals from the user. The photoplethysmogram signals are extracted from user's peripheral body parts selected from a group comprising but not limited to finger, ear, and toe. In a specific embodiment, the photoplethysmogram signals are extracted from user's forehead. The mobile communication device (204) captures photoplethysmogram signal in reflective mode. The mobile communication device (204) is selected from a group comprising of smart phone, mobile phone, laptop, tablet, and personal digital assistant.

The image capturing device (202) coupled with the mobile communication device (204) is a camera and have a light emitting source for extracting photoplethysmogram signals from the user's peripheral body parts selected from a group comprising but not limited to finger, ear, toe; forehead thereby, obtaining a video sequence of the light, reflected from user's peripheral body parts. The periodic nature of photoplethysmogram signal is caused due to varying intensity of redness in the region of interest (ROI) of each video frame. However, Android APIs provide the camera preview information in Y $C_B C_R$ colorspace. Thus further conversion to RGB domain in real time causes additional computation in the mobile communication device (204) which may reduce the frame rate of the captured video. Since the intensity information is carried in the luminescence part of Y $C_B C_R$, the image capturing device (202) coupled with the mobile communication device (204) is extracting the photoplethysmogram signals in Y domain of Y $C_B C_R$ color space of a captured video. The value of photoplethysmogram signal corresponding to $1^{th}$ frame of a video of W×H resolution is represented by the mean Y value of that frame, as:

$$PPG(l) = \frac{\sum_{i=1}^{W}\sum_{j=1}^{H} Y_{i,j}}{W*H}$$

In another embodiment of the present invention, the photoplethysmogram signals are extracted as a time series data wherein signal value of photoplethysmogram at $n^{th}$ frame is represented by mean value of Y component of the $n^{th}$ frame.

In another embodiment of the present invention, the up sampling module (206) is adapted for up sampling the extracted photoplethysmogram signals. The extracted photoplethysmogram signals are up sampled to a uniform sampling rate using linear interpolation. The image capturing device (202) coupled with the mobile communication device (204) extracts photoplethysmogram signals from the user's peripheral body parts as a video stream at 30 fps, yielding a very low sampling rate of the extracted photoplethysmogram signal (30 Hz) compared to clinical devices (100 Hz or more). Linear interpolation is applied to the extracted photoplethysmogram signals for up sampling of extracted photoplethysmogram signals to a uniform sampling rate.

In another embodiment of the present invention, the filtering module (208) is adapted for filtering the up sampled photoplethysmogram signals.

The photoplethysmogram signal contains a slowly varying DC and several high frequency noise components. However, the fundamental frequency lies between 1 to 1.5 Hz based on the heart rate of a person (60-90 bpm). The up sampled photoplethysmogram signals are shifted to its zero mean and applied to a 4th order Butterworth band-pass filter having cutoff frequencies of 0.5 Hz and 5 Hz to remove the undesired frequency components.

Figure 3:
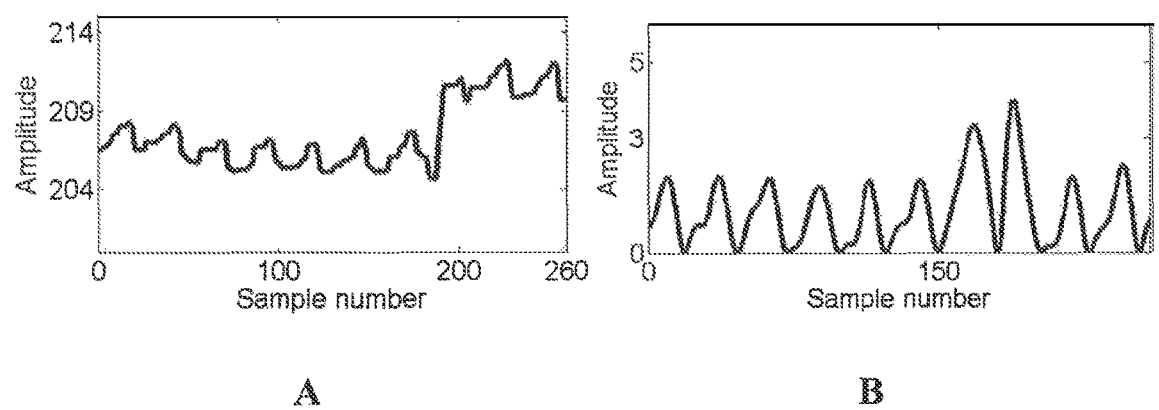
FIG. 3: shows a graphical representation for removing uneven baseline drift of each cycle of the up sampled and filtered photoplethysmogram signals.

Referring to FIG. 3 is a graphical representation for removing uneven baseline drift of each cycle of the up sampled and filtered photoplethysmogram signals, wherein the shape of a typical photoplethysmogram waveform captured using mobile communication device (204) is too noisy for time domain analysis which can be seen in FIG. 3 A.

In another embodiment of the present invention, the baseline drift removal module (210) is adapted for removing uneven baseline drift of each cycle of the up sampled and filtered photoplethysmogram signals. According to FIG. 3 A, photoplethysmogram signal may not have a fixed baseline. Moreover, both ends of a single photoplethysmogram cycle may not often aligned. The unequal baseline of photoplethysmogram signal is a major reason for wrong feature calculation. For a uniform sampled photoplethysmogram signal, if F be a vector containing all the k samples in a cycle, a second vector T forming a line segment between the two endpoints of that cycle is constructed, with k-2 equally spaced values in between, generated using linear interpolation. The vector $F^1=T-T$ represents the modified cycle with zero baseline. The same is done for all other photoplethysmogram cycles as well. The effect of pre-processing of the photoplethysmogram signals using the up sampling module (206) and the filtering module (208), thereafter baseline removal algorithm on the noisy signal using the baseline drill removal module (210) is shown in FIG. 3 B, making it cleaner for further analysis.

In another embodiment of the present invention, the outlier removing module (212) is adapted for removing outlier cycles of the photoplethysmogram signals by k-means clustering.

The composite feature set includes a combination of features, extracted from each cycle of the original photoplethysmogram signal as well as the modeled photoplethysmogram signal. Thus, removal of outlier cycles, caused due to inaccurate detection of troughs is necessary before applying the features to the ANN structures. The outlier cycles of the photoplethysmogram signals are removed by splitting each cycle of the photoplethysmogram signals into a plurality of rectangular overlapping windows of equal size. If the signal is assumed to be stationary, mean of dominant peak locations in all the windows' spectrum indicates its fundamental frequency $f_c$, so ideal time period. becomes $T_{cideal}=1=f_c$. Thereby identifying fundamental frequency of the plurality of rectangular overlapping windows. Further, absolute difference from ideal time period is calculate, indicating high value of the ideal time period as a wrongly detected cycle. For all the cycles, absolute difference from ideal time period as $\Delta T_c=|Tc-T_{cideal}|$. A high value of $\Delta T_c$ indicates a wrongly detected cycle. K-Means clustering (K=2) approach is used to remove such outlier cycles. First, histogram analysis is done for all $\Delta T_c$ to initialize the cluster centroids, followed by 2-Means clustering and estimating of cluster density to remove the outliers. Centroid of the histogram bin having maximum entries is considered as the initial centroid (C1) for one cluster. The initial centroid of the other cluster (C2) is the farthest data point from C1. K-Means algorithm is used to get the final cluster centroids. Entries corresponding to the centroid with lower Xie-Beni index are considered to be compact and those cycles are used for feature extraction.

Figure 4:
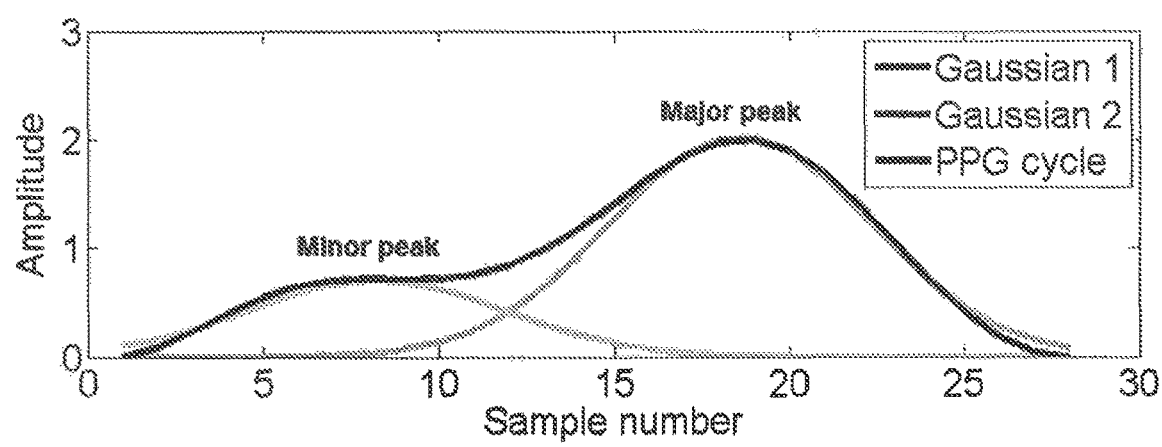
FIG. 4: shows a graphical representation for modeling remaining cycles of the photoplethysmogram signals after removing outlier cycles with a sum of 2 Gaussian functions.

Referring to FIG. 4 a graphical representation for modeling remaining cycles of the photoplethysmogram signals after removing outlier cycles with a sum of 2 Gaussian functions is presented.

In another embodiment of the present invention, the signal modeling module (214) is adapted for modeling remaining cycles of the photoplethysmogram signals after removing outlier cycles with a sum of 2 Gaussian functions. As mentioned earlier, photoplethysmogram signals captured using the mobile communication device (204) are extremely noise-prone and contains several irregularities in shape due to that. Thus, a mathematical modeling may ensure better signal realization for analysis. Given a set of uniformly spaced single valued data, they can be approximated by a sum of Gaussian functions with some accuracy. According to FIG. 3 B, photoplethysmogram cycle closely follows a Gaussian shape. However it is asymmetric in nature and contains two peaks, where the major and prominent peak represents the systolic peak and the minor peak represents the diastolic peak. Thus, instead of a single Gaussian, a sum of 2 Gaussian functions may fit the shape with better accuracy. If $\{x_k: k=1, 2 \ldots N\}$ be a set of equally spaced data points with corresponding photoplethysmogram signal amplitude of $\{PPG_k: k=1, 2 \ldots N\}$, then the approximation of $PPG_k$ is done with yk, as given in following equation:

$$y_k = a_1 e^{\frac{-(k-b_1)^2}{2c_1^2}} + a_2 e^{\frac{-(k-b_2)^2}{2c_2^2}} \text{ for } k = 1, 2, \ldots N$$

by optimizing the constants $a_1$, $b_1$, $c_1$, $a_2$, $b_2$, $c_2$ so that the cost function ($h_k$) in following equation gets minimized:

$$h_k = \sqrt{\frac{1}{N}\sum_{k=1}^{N}(PPG_k - y_k)^2}$$

A typical photoplethysmogram cycle, fitted using a sum of 2 Gaussian curves are shown in FIG. 4. The Root Mean Square Error (RMSE) is a popular tool in statistics to measure the goodness of a curve fitting, typically a lower value indicates a better fitting. The RMSE between the original cycle and the modeled cycle, fitted with 2 Gaussian curves is found to be 1.5%. Whereas, RMSE for the same cycle, becomes 8.3% and 3.6% respectively, if fitted with a single Gaussian or a Weibull function. For more comprehensive performance analysis, a second waveform is considered, containing different possible shapes of photoplethysmogram pulse and fit each of them with a sum of 2 Gaussian functions.

Figure 5:
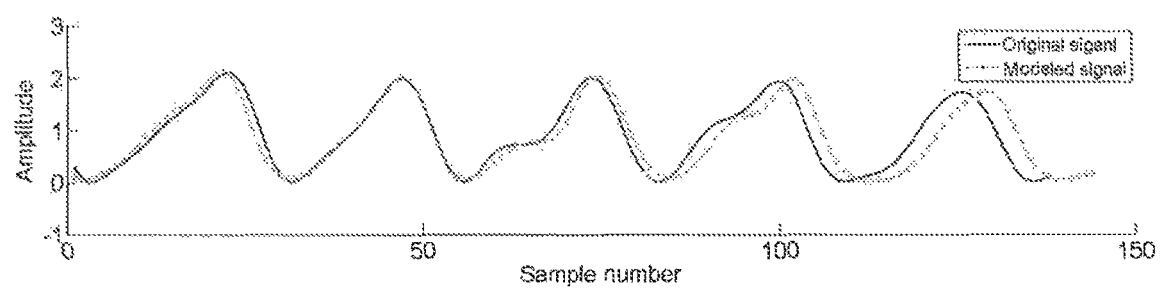
FIG. 5: shows a graphical representation for comparing originally extracted and modeled photoplethysmogram signals.

Referring to FIG. 5 is a graphical representation for comparing originally extracted and modeled photoplethysmogram signals. It can be observed that the proposed curve fitting methodology works well for the entire signal. The RMSE between the actual and modeled photoplethysmogram signal becomes less than 2.5%, indicating its feasibility to fit any kind of PPG signal with commending accuracy, The constant parameter a indicates the height of the peak, b is the position of the center of the peak and c controls the width of the curve, thus some of these model parameters are used as additional PPG features for analysis.

In another embodiment of the present invention, the feature extraction module (216) is adapted for extracting time domain features from originally extracted and modeled photoplethysmogram signals for estimating blood pressure of the user. The time domain features including systolic time ($T_s$); diastolic time ($T_d$); pulse-width at; 33% ($B_{33}$); 75% ($B_{75}$) of pulse height ($T_c$); total pulse width of the original signal, along with Gaussian RMS width; $C_1$; $C_2$ of the fitted Gaussian curves to create composite feature vector in $R^7$ feature space; and mode parameters b1 and b2 are extracted from originally extracted and modeled photoplethysmogram signals for estimating blood pressure of the user using machine learning techniques.

In another embodiment of the present invention, according to the following equation:

$$P_s = P(t \mid t = T_s)$$
$$= P_d e^{-T_s/RC} + \frac{I_0 T_s C \pi R^2}{T_s^2 + C^2 \pi^2 R^2}(1 + e^{-T_s/RC})$$

$$P_d = P(t \mid t = T_c) = P_s e^{-T_d/RC}$$

Systolic (Ps) and diastolic (Pd) blood pressure $I_0$, systolic time (Ts), diastolic time (Td), R and C. Ts and Td can be calculated from PPG signal. Assume cardiac output (CO) of a person to be fixed 5 lit/minute. I0 can be calculated from the below equation:

$$I_0 = \frac{C_o T_c}{60 \int_0^{T_s} \sin\left(\frac{\pi t}{T_s}\right) dt}$$

Since, R and C does not have any mathematical relationship with photoplethysmogram features. Artificial Neural Network (ANN) based machine learning approach is used to estimate R and C from photoplethysmogram features. The estimation of R and C and consequently blood pressure of the user using photoplethysmogram signals further has training and testing phases.

Figure 6:
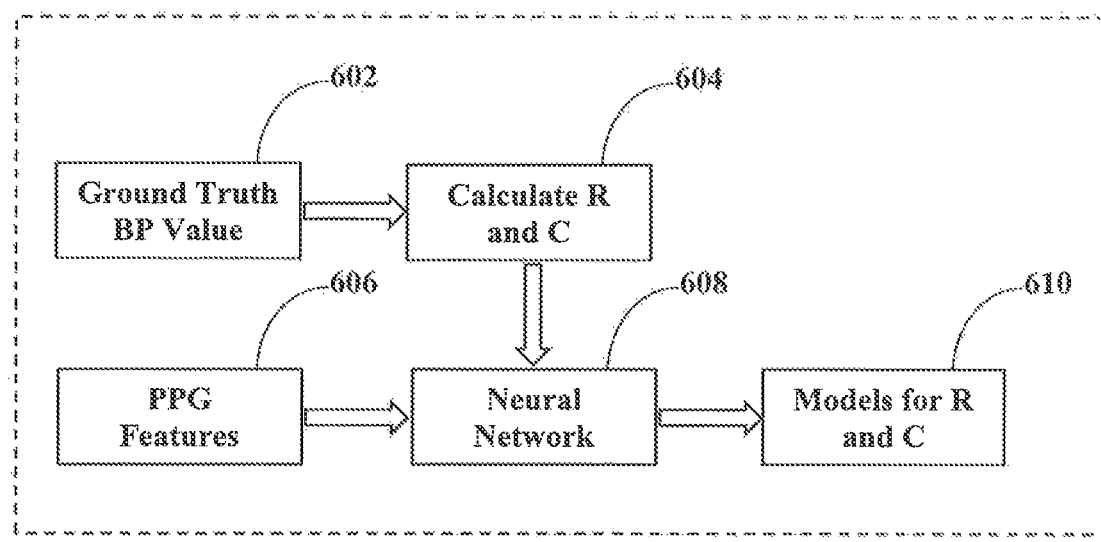
FIG. 6A and FIG. 6B: shows a block diagram illustrating training phase and testing phase for estimating blood pressure of a user using photoplethysmogram signals.
Figure 6:
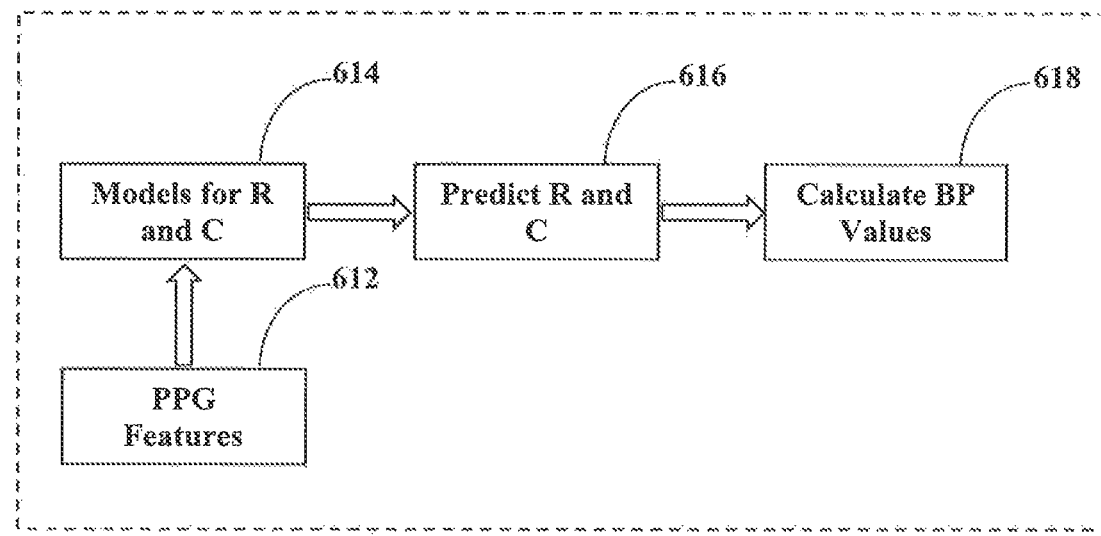

Referring to FIG. 6 A is a block diagram illustrating training phase for estimating blood pressure of a user using photoplethysmogram signals.

In another embodiment of the present invention, training models are created for R and C, wherein around 100 users with known blood pressure are used for training phase. The ground truth blood pressure value (602), systolic (Ps) and diastolic (Pd) blood pressure is known for said users. R and C is calculated (604) using ground truth blood pressure value (602) by reversing systolic (Ps) and diastolic (Pei) blood pressure equations. The systolic time (Ts), diastolic time (Td) and CO can be measured for said users using respective photoplethysmogram signals (606). The training models (610) for R and C are generated by running Artificial Neural Network (ANN) (608) offline and said generated training models for R and C are stored.

Referring to FIG. 6 B is a block diagram illustrating testing phase for estimating blood pressure of a user using photoplethysmogram signals.

In another embodiment of the present invention, the testing phase runs on user's mobile communication device (204) in real time for estimating blood pressure of a user using photoplethysmogram signals. The generated training models for R and C during training phase are stored in the mobile communication device (204) where the testing phase of the application runs. When a user runs the application on its mobile communication device (204), photoplethysmogram signals are extracted from the user. The systolic time (Ts), diastolic time (Td) and $I_o$ are calculated. The R and C are estimated/predicted (616) for the user from photoplethysmogram features (612) and training models (614). Upon estimating R and C, systolic (Ps) and diastolic (Pd) blood pressure are calculated (618) using systolic (Ps) and diastolic (Pd) blood pressure equations.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for noise cleaning of photoplethysmogram (PPG) signals for estimating blood pressure (BP) of a user; said method comprising:
   a. extracting, via one or more hardware processors, photoplethysmogram signals from the user using an image capturing device (202) coupled with a mobile communication device (204);
   b. up sampling, via one or more hardware processors, the extracted photoplethysmogram signals using an up sampling module (206);
   c. filtering, via one or more hardware processors, the up sampled photoplethysmogram signals using a filtering module (208);
   d. removing, via one or more hardware processors, uneven baseline drift of each cycle of the up sampled and filtered photoplethysmogram signals using a baseline drift removal module (210);
   e. removing, via one or more hardware processors, outlier cycles of the photoplethysmogram signals by k-means clustering using an outlier removing module (212);
   f. modeling, via one or more hardware processors, remaining cycles of the photoplethysmogram signals after removing outlier cycles with a sum of 2 Gaussian functions using a signal modeling module (214); and
   g. extracting, via one or more hardware processors, time domain features from originally extracted and modeled photoplethysmogram signals using a feature extraction module (216) for estimating blood pressure of the user.

2. The method as claimed in claim 1, wherein the photoplethysmogram signals are extracted from user's peripheral body parts selected from a group comprising finger, ear, toe and forehead.

3. The method as claimed in claim 1, wherein the photoplethysmogram signals are extracted from the user using a light emitting source attached to the image capturing device coupled with the mobile communication device.

4. The method as claimed in claim 1, wherein the photoplethysmogram signals are extracted in Y domain of $YC_BC_R$ color space of a captured video using the image capturing device coupled with the mobile communication device.

5. The method as claimed in claim 1, wherein the image capturing device coupled with the mobile communication device extracts photoplethysmogram signals as a video stream at 30 fps.

6. The method as claimed in claim 1, wherein the photoplethysmogram signals are extracted as a time series data wherein signal value of photoplethysmogram at $n^{th}$ frame is represented by mean value of Y component of the $n^{th}$ frame.

7. The method as claimed in claim 1, wherein the extracted photoplethysmogram signals are up sampled using linear interpolation.

8. The method as claimed in claim 1, wherein the up sampled photoplethysmogram signals are shifted to its zero mean and applied to a 4th order Butterworth band-pass filter having cutoff frequencies of 0.5 Hz and 5 Hz.

9. The method as claimed in claim 1, wherein the uneven baseline drift of each cycle (F) of the up sampled and filtered photoplethysmogram signals of length k is removed by constructing a second vector T forming a line segment of length k, having endpoints of the second vector T same as the endpoints of each cycle F, along with k-2 equal spaced points in between constructed using linear regression, where the vector F1=F−T representing the modified cycle with zero baseline.

10. The method as claimed in claim 1, wherein the outlier cycles of the photoplethysmogram signals are removed by splitting each cycle of the photoplethysmogram signals into a plurality of rectangular overlapping windows of equal size, identifying fundamental frequency of the plurality of rectangular overlapping windows, calculating absolute difference from ideal time period, indicating high value of the ideal time period as a wrongly detected cycle, removing wrongly detected outliers using k-means clustering.

11. The method as claimed in claim 1, wherein the time domain features including systolic time; diastolic time; pulse-width at; 33% (B33); 75% (B75) of pulse height; total pulse width of the original signal, along with Gaussian RMS width; $C_1$; $C_2$ of the fitted Gaussian curves; and mode parameters b1 and b2 are extracted from originally extracted and modeled photoplethysmogram signals for estimating blood pressure of the user using machine learning techniques.

12. A system for noise cleaning of photoplethysmogram (PPG) signals for estimating blood pressure (BP) of a user; said system comprising:
   a. an image capturing device coupled with a mobile communication device, adapted for extracting photoplethysmogram signals from the user;
   b. an up sampling module, adapted for up sampling the extracted photoplethysmogram signals;
   c. a filtering module, adapted for filtering the up sampled photoplethysmogram signals;
   d. a baseline drift removal module, adapted for removing uneven baseline drift of each cycle of the up sampled and filtered photoplethysmogram signals;
   e. an outlier removing module, adapted for removing outlier cycles of the photoplethysmogram signals by k-means clustering;
   f. a signal modeling module, adapted for modeling remaining cycles of the photoplethysmogram signals after removing outlier cycles with a sum of 2 Gaussian functions; and
   g. a feature extraction module, adapted for extracting time domain features from originally extracted and modeled photoplethysmogram signals for estimating blood pressure of the user.

13. The system as claimed in claim 12, wherein the image capturing device coupled with a mobile communication device is adapted to extract photoplethysmogram signals from user's peripheral body parts selected from a group comprising finger, ear, toe and forehead.

14. The system as claimed in claim 12, wherein the image capturing device coupled with the mobile communication device is having a light emitting source for extracting photoplethysmogram signals.

15. The system as claimed in claim 12, wherein the image capturing device coupled with the mobile communication device is extracting the photoplethysmogram signals in Y domain of $YC_BC_R$ color space of a captured video.

16. The system as claimed in claim 12, wherein the image capturing device coupled with the mobile communication device extracts photoplethysmogram signals as a video stream at 30 fps.

17. The system as claimed in claim 12, wherein the photoplethysmogram signals are extracted as a time series data wherein signal value of photoplethysmogram at $n^{th}$ frame is represented by mean value of Y component of the $n^{th}$ frame.

18. The system as claimed in claim 12, wherein the extracted photoplethysmogram are up sampled using linear interpolation.

19. The system as claimed in claim 12, wherein the up sampled photoplethysmogram signals are shifted to its zero mean and applied to a 4th order Butterworth band-pass filter having cutoff frequencies of 0.5 Hz and 5 Hz.

20. The system as claimed in claim 12, wherein the uneven baseline drift of each cycle (F) of the up sampled and filtered photoplethysmogram signals of length k is removed by constructing a second vector T forming a line segment of length k, having endpoints of the second vector T same as the endpoints of each cycle F, along with k-2 equal spaced points in between constructed using linear regression, where the vector F1=F−T representing the modified cycle with zero baseline.

21. The system as claimed in claim 12, wherein the outlier cycles of the photoplethysmogram signals are removed by splitting each cycle of the photoplethysmogram signals into a plurality of rectangular overlapping windows of equal size, identifying fundamental frequency of the plurality of rectangular overlapping windows, calculating absolute difference from ideal time period, indicating high value of the ideal time period as a wrongly detected cycle, removing wrongly detected outliers using k-means clustering.

22. The system as claimed in claim 12, wherein the time domain features including systolic time; diastolic time pulse-width at; 33% (B33); 75% (B75) of pulse height; total pulse width of the original signal, along with Gaussian RMS width; $C_1$; $C_2$ of the fitted Gaussian curves; and mode parameters b1 and b2 are extracted from originally extracted and modeled photoplethysmogram signals for estimating blood pressure of the user using machine learning techniques.

23. A non-transitory computer-readable medium having embodied thereon a computer program for executing a method comprising:
   a. extracting photoplethysmogram signals from the user using an image capturing device coupled with a mobile communication device;
   b. up sampling the extracted photoplethysmogram signals using an up sampling module;
   c. filtering the up sampled photoplethysmogram signals using a filtering module;
   d. removing uneven baseline drift of each cycle of the up sampled and filtered photoplethysmogram signals using a baseline drift removal module;
   e. removing outlier cycles of the photoplethysmogram signals by k-means clustering using an outlier removing module;
   f. modeling remaining cycles of the photoplethysmogram signals after removing outlier cycles with a sum of 2 Gaussian functions using a signal modeling module; and
   g. extracting time domain features from originally extracted and modeled photoplethysmogram signals using a feature extraction module for estimating blood pressure of the user.

* * * * *